US011666062B2

United States Patent
Heining et al.

(10) Patent No.: US 11,666,062 B2
(45) Date of Patent: Jun. 6, 2023

(54) OIL COMPRISING AT LEAST ONE POLYUNSATURATED FATTY ACID HAVING AT LEAST 20 CARBON ATOMS (LC-PUFA)

(71) Applicants: DSM IP ASSETS B.V., Heerlen (NL); EVONIK OPERATIONS GMBH, Essen (DE)

(72) Inventors: Martin Heining, Karlstein am Main (DE); Vinod Tarwade, Kaiseraugst (CH); Viktor Stefan Wallimann, Kaiseraugst (CH)

(73) Assignees: DSM IP ASSETS B.V., Heerlen (NL); EVONIK OPERATIONS GMBH, Essen (DE)

( * ) Notice: Subject to any disclaimer, the term of this patent is extended or adjusted under 35 U.S.C. 154(b) by 157 days.

(21) Appl. No.: 16/956,820

(22) PCT Filed: Dec. 19, 2018

(86) PCT No.: PCT/EP2018/086009
§ 371 (c)(1),
(2) Date: Jun. 22, 2020

(87) PCT Pub. No.: WO2019/122031
PCT Pub. Date: Jun. 27, 2019

(65) Prior Publication Data
US 2020/0404938 A1    Dec. 31, 2020

(30) Foreign Application Priority Data
Dec. 22, 2017 (EP) ..................... 17210142

(51) Int. Cl.
*A23D 9/007* (2006.01)
*A23K 20/158* (2016.01)
*C11B 1/10* (2006.01)
*C12N 1/00* (2006.01)

(52) U.S. Cl.
CPC ............ *A23D 9/007* (2013.01); *A23K 20/158* (2016.05); *C11B 1/108* (2013.01); *C12N 1/005* (2013.01)

(58) Field of Classification Search
CPC ...... A23D 9/007; A23K 20/158; C11B 1/108; C12N 1/005
See application file for complete search history.

(56) References Cited

U.S. PATENT DOCUMENTS

2011/0295028 A1* 12/2011 Cherinko .................. C11B 3/02
554/175

FOREIGN PATENT DOCUMENTS

| WO | 2013/013211 | 1/2013 | |
|---|---|---|---|
| WO | 2015/095690 | 6/2015 | |
| WO | 2015/095694 | 6/2015 | |
| WO | 2015/095696 | 6/2015 | |
| WO | WO-2015095690 A2 * | 6/2015 | ............ C07C 51/48 |
| WO | WO-2015095694 A1 * | 6/2015 | ............ C07C 51/42 |
| WO | WO-2015095696 A1 * | 6/2015 | ............... A23D 9/00 |
| WO | 2018/011275 | 1/2018 | |
| WO | 2018/011286 | 1/2018 | |

OTHER PUBLICATIONS

International Search Report for PCT/EP2018/086009 dated Mar. 14, 2019, 5 pages.
Written Opinion of the ISA for PCT/EP2018/086009 dated Mar. 14, 2019, 5 pages.

* cited by examiner

*Primary Examiner* — Deborah D Carr
(74) *Attorney, Agent, or Firm* — Nixon & Vanderhye P.C.

(57) ABSTRACT

The present invention relates to an oil comprising at least one polyunsaturated fatty acid having at least 20 carbon atoms (LC-PUFA). It is found that LC-PUFA-containing oil are susceptible to gelling by formation of microscopic crystals during storage ultimately resulting in unfavorable quality and handling properties. This problem has been particularly observed with a microbial oil comprising at least about 25% by weight LC-PUFA and a moisture content of 0.2 to 5% by weight. Surprisingly, it has been found that a LC-PUFA-containing oil as described above is effectively stable and does not show gelling properties under conventional storage conditions, if the oil composition as such contains less than about 8% preferably less than about 5% by weight of free fatty acid in the residual moisture of the oil. Therefore, the present invention is directed to an oil comprising at least about 25% by weight LC-PUFA and a moisture content comprising less than about 8% preferably less than about 5% by weight of free fatty acid.

11 Claims, No Drawings

US 11,666,062 B2

OIL COMPRISING AT LEAST ONE POLYUNSATURATED FATTY ACID HAVING AT LEAST 20 CARBON ATOMS (LC-PUFA)

This application is the U.S. national phase of International Application No. PCT/EP2018/086009 filed Dec. 19, 2018 which designated the U.S. and claims priority to EP Patent Application No. 17210142.0 filed Dec. 22, 2017, the entire contents of each of which are hereby incorporated by reference.

The present invention relates to an oil comprising at least one polyunsaturated fatty acid having at least 20 carbon atoms (LC-PUFA).

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

Polyunsaturated fatty acids (PUFAs) are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 long chain polyunsaturated fatty acid (LC-PUFA) with a chain length of 22 carbons and 6 double bonds, often designated as "22:6 n-3." Other omega-3 LC-PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 LC-PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates.

Flaxseed oil and fish oils are considered good dietary sources of omega-3 fatty acids. Flaxseed oil contains no EPA, DHA, DPA, or ARA but rather contains linolenic acid (CI 8:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

LC-PUFAs can be produced by micro-organisms in a fermentation process. LC-PUFAs can also be produced in plants. For instance, WO 2006/085672 describes a process for the production of a LC-PUFA containing microbial biomass from which a microbial oil according to the invention can be isolated.

A microbial oil of the invention is a "crude oil" or a "refined oil" comprising a triacylglycerol fraction of at least about 35% by weight. A "crude oil" is an oil that is extracted from the biomass of the microorganism without further processing. A "refined oil" is an oil that is obtained, by treating a crude oil with standard processing of refining, bleaching, and/or deodorizing. See, e.g., U.S. Pat. No. 5,130,242, incorporated by reference herein in its entirety. A microbial oil also includes a "final oil" as described herein, which is a refined oil that has been diluted with a vegetable oil. In some embodiments, a final oil is a refined oil that has been diluted with high oleic sunflower oil. The term "microbial" as used herein includes, but is not limited to, the terms "microalgal," "thraustochytrid," and taxonomic classifications associated with any of the microorganisms described herein.

Thraustochytrids are microorganisms of the order Thraustochytriales. Thraustochytrids include members of the genus *Schizochytrium* and *Thraustochytrium* and have been recognized as an alternative source of omega-3 fatty acids, including DHA and EPA. See U.S. Pat. No. 5,130,242. Oils produced from these marine heterotrophic microorganisms often have simpler polyunsaturated fatty acid profiles than corresponding fish or microalgal oils. Lewis, T. E., Mar. Biotechnol. 1: 580-587 (1999). Strains of thraustochytrid species have been reported to produce omega-3 fatty acids as a high percentage of the total fatty acids produced by the organisms. U.S. Pat. No. 5,130,242; Huang, J. et al, J. Am. Oil. Chem. Soc. 78: 605-610 (2001); Huang, J. et al., Mar. Biotechnol. 5: 450-457 (2003). However, isolated thraustochytrids may vary in the identity and amounts of LC-PUFAs produced.

In some embodiments, a fatty acid as described herein can be a fatty acid ester. In some embodiments, a fatty acid ester includes an ester of an omega-3 fatty acid, omega-6 fatty acid, and combinations thereof. In some embodiments, the fatty acid ester is a DHA ester, an EPA ester, or a combination thereof. In some embodiments, an oil or fraction thereof as described herein is esterified to produce an oil or fraction thereof comprising fatty acid esters. The term "ester" refers to the replacement of the hydrogen in the carboxylic acid group of the fatty acid molecule with another substituent. Typical esters are known to those in the art, a discussion of which is provided by Higuchi, T. and V. Stella in Pro-drugs as Novel Delivery Systems, Vol. 14, A.C.S. Symposium Series, Bioreversible Carriers in Drug Design, Ed. Edward B. Roche, American Pharmaceutical Association, Pergamon Press, 1987, and Protective Groups in Organic Chemistry, McOmie ed., Plenum Press, New York, 1973. Examples of esters include methyl, ethyl, propyl, butyl, pentyl, t-butyl, benzyl, nitrobenzyl, methoxybenzyl, benzhydryl, and trichloroethyl. In some embodiments, the ester is a carboxylic acid protective ester group, esters with aralkyl (e.g., benzyl, phenethyl), esters with lower alkenyl (e.g., allyl, 2-butenyl), esters with lower-alkoxy-lower-alkyl (e.g., methoxymethyl, 2-methoxyethyl, 2-ethoxyethyl), esters with lower-alkanoyloxy-lower-alkyl (e.g., acetoxymethyl, pivaloyloxymethyl, 1-pivaloyloxyethyl), esters with lower-alkoxycarbonyl-lower-alkyl (e.g., methoxycarbonylmethyl, isopropoxycarbonylmethyl), esters with carboxy-lower alkyl (e.g., carboxymethyl), esters with lower-alkoxycarbonyloxy-lower-alkyl (e.g., 1-(ethoxycarbonyloxy)ethyl, 1-(cyclohexyloxycarbonyloxy)ethyl), esters with carbamoyloxy-lower alkyl (e.g., carbamoyloxymethyl), and the like. In some embodiments, the added substituent is a linear or cyclic hydrocarbon group, e.g., a C1-C6 alkyl, C1-C6 cycloalkyl, C1-C6 alkenyl, or C1-C6 aryl ester. In some embodiments, the ester is an alkyl ester, e.g., a methyl ester, ethyl ester or propyl ester. In some embodiments, the ester substituent is added to the free fatty acid molecule when the fatty acid is in a purified or semi-purified state. Alternatively, the fatty acid ester is formed upon conversion of a triacylglycerol to an ester.

It is found that LC-PUFA-containing oil are susceptible to gelling by formation of microscopic crystals during storage ultimately resulting in unfavorable quality and handling properties. This problem has been particularly observed with a microbial oil comprising at least about 25% by weight LC-PUFA and a moisture content of 0.2 to 5% by weight, in particular 0.5 to 2%.

Although, sharing the oil may help to destroy the crystals—at least for a short term—which would lead to a non-gelling oil, it is a need to avoid the formation of microscopic crystals in the oil.

Surprisingly, it has been found that a LC-PUFA-containing oil is effectively stable and does not show gelling properties as described above under conventional storage conditions, if the oil composition as such contains less than about 8% preferably less than about 5% by weight of free fatty acid in the residual moisture of the oil.

Therefore, the present invention is directed to an oil comprising at least about 25% by weight LC-PUFA and a moisture content comprising less than about 8%, preferably less than about 5% by weight of free fatty acid. In some embodiments, the microbial oil further comprises at least about 25% by weight docosahexaenoic, at least about 10% by weight eicosapentaenoic acid and a moisture content of less than 2%, preferably less than 1% by weight.

The oil according to the invention is an oil derived from a microbial organism or a plant.

The microbial organisms which contain a PUFAs containing lipid are described extensively in the prior art. The cells used may, in this context, in particular be cells which already naturally produce PUFAs (polyunsaturated fatty acids); however, they may also be cells which, as the result of suitable genetic engineering methods or due to random mutagenesis, show an improved production of PUFAs or have been made capable of producing PUFAs, at all. The production of the PUFAs may be auxotrophic, mixotrophic or heterotrophic.

The cells according to the invention are preferably selected from algae, fungi, particularly yeasts, bacteria, or protists. The cells are more preferably microbial algae or fungi.

Suitable cells of oil-producing yeasts are, in particular, strains of *Yarrowia, Candida, Rhodotorula, Rhodosporidium, Cryptococcus, Trichosporon* and *Lipomyces.*

Suitable cells of oil-producing microalgae and algae-like microorganisms are, in particular, microorganisms selected from the phylum Stramenopiles (also called Heterokonta). The microorganisms of the phylum Stramenopiles may in particular be selected from the following groups of microorganisms: Hamatores, Proteromonads, Opalines, Developayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinales, Pedinellales, Dictyochales), Chrysomeridales, Sarcinochrysidales, Hydrurales, Hibberdiales, and Chromulinales. Other preferred groups of microalgae include the members of the green algae and dinoflagellates, including members of the genus Crypthecodium.

The plant cells may in particular be selected from cells of the families Brassicaceae, Elaeagnaceae and Fabaceae. The cells of the family Brassicaceae may be selected from the genus *Brassica*, in particular from oilseed rape, turnip rape and Indian mustard; the cells of the family Elaeagnaceae may be selected from the genus *Elaeagnus*, in particular from the species *Oleae europaea*; the cells of the family Fabaceae may be selected from the genus Glycine, in particular from the species *Glycine max*.

In some embodiments, the total amount of omega-3 polyunsaturated fatty acids in the oil is at least about 400 mg per one gram of oil.

In other embodiments, the total amount of omega-3 polyunsaturated fatty acids in the oil is at least about 500 mg per one gram of oil.

In still further embodiments, the total amount of omega-3 polyunsaturated fatty acids in the oil is from about 400 mg to about 800 mg per one gram of oil.

In some embodiments, the oil comprises from about 100 mg to about 300 mg EPA per one gram of oil and from about 200 mg to about 500 mg DHA per one gram of oil.

In a still further embodiment, the oil comprises from about 100 mg to about 250 mg EPA per one gram of oil; from about 250 mg to about 400 mg DHA per one gram of oil.

In some embodiments, the oil comprises a ratio of EPA:DHA of 1:1 to 1:30 or 1:1 to 1:5 by weight of total omega-3 polyunsaturated fatty acids.

In some embodiments, the oil comprises a ratio of EPA:DHA of 1:1 to 1:4 by weight of total omega-3 polyunsaturated fatty acids.

In some embodiments, the oil comprises a ratio of EPA:DHA of at least 1:1, at least 1:2, at least 1:3, or at least 1:4 by weight of total omega-3 polyunsaturated fatty acids.

In some embodiments, the oil is a microbial oil comprising at least about 25% by weight docosahexaenoic acid, at least about 10% by weight eicosapentaenoic acid, a moisture content of less than 2%, preferably less than 1% by weight and a less than 5% by weight free fatty acids in the moisture.

The present invention is also directed to a microbial oil comprising a triacylglycerol fraction of at least about 10% by weight, wherein at least about 12% by weight of the fatty acids in the triacylglycerol fraction is eicosapentaenoic acid, wherein at least about 25% by weight of the fatty acids in the triacylglycerol fraction is docosahexaenoic acid, and wherein less than about 5% by weight of the fatty acids in the triacylglycerol fraction is arachidonic acid.

In some embodiments, the microbial oil comprises a sterol esters fraction of about 0%, at least about 0.1%, at least about 0.2%, at least about 0.5%, at least about 1%, at least about 1.5%, at least about 2%, or at least about 5% by weight. In some embodiments, the microbial oil comprises a sterol esters fraction of about 0% to about 1.5%, about 0% to about 2%, about 0% to about 5%, about 1% to about 1.5%, about 0.2% to about 1.5%, about 0.2% to about 2%, or about 0.2% to about 5% by weight. In some embodiments, the microbial oil comprises a sterol esters fraction of about 5% or less, about 4% or less, about 3% or less, about 2% or less, about 1% or less, about 0.5% or less, about 0.3% or less, about 0.2% or less, about 0.5% or less, about 0.4% or less, about 0.3% or less, or about 0.2% or less by weight.

In some embodiments, the microbial oil comprises a triacylglycerol fraction of at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some embodiments, the microbial oil comprises a triacylglycerol fraction of about 35% to about 98%, about 35% to about 90%, about 35% to about 80%, about 35% to about 70%, about 35% to about 70%, about 35% to about 65%, about 40% to about 70%, about 40% to about 65%, about 40% to about 55%, about 40% to about 50%, about 65% to about 95%, about 75% to about 95%, about 75% to about 98%, about 80% to about 95%, about 80% to about 98%, about 90% to about 96%, about 90% to about 97%, about 90% to about 98%, about 90%, about 95%, about 97%, or about 98% by weight.

In some embodiments, the microbial oil comprises a diacylglycerol fraction of at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 10% to about 45%, about 10% to about 40%, about 10% to about 35%, about 10% to about 30%, about 15% to about 40%, about 15% to about 35%, or about 15% to about 30% by weight. In some embodiments, the microbial oil comprises a 1,2-diacylglycerol fraction of at least about 0.2%, at least about 0.3%, at least about 0.4%, at least about 0.5%, at least about 1%, at least about 5%, at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 0.2% to about 45%, about 0.2% to about 30%, about 0.2% to about 20%, about 0.2% to about 10%, about 0.2% to about 5%, about 0.2% to about 1%, about 0.2% to about 0.8%, about 0.4% to about 45%, about 0.4% to about 30%, about 0.4% to about 20%, about 0.4% to about 10%, about 0.4% to about 5%, about 0.4% to about 1%, about 0.4% to about 0.8%, about 0.5% to about 1%, about 0.5% to about 0.8%, about 10% to about 45%, about 10% to about 40%, about 10% to about 35%, about 10% to about 30%, about 15% to about 40%, about 15% to about 35%, about 15% to about 30%, or about 15% to about 25% by weight. In some embodiments, the microbial oil comprises a 1,3-diacylglycerol fraction of at least about 0.1%, at least about 0.2%, at least about 0.5%, at least about 1%, at least about 2%, at least about 2.5%, or at least about 3% by weight. In some embodiments, the microbial oil comprises a sterol fraction of at least about 0.3%, at least about 0.4%, at least about 0.5%, at least about 1%, at least about 1.5%, at least. about 2%, or at least about 5% by weight.

In some embodiments, the microbial oil comprises a sterol fraction of about 0.3% to about 5%, about 0.3% to about 2%, about 0.3% to about 1.5%, about 0.5% to about 1.5%, about 1% to about 1.5%, about 0.5% to about 2%, about 0.5% to about 5%, about 1% to about 2%, or about 1% to about 5% by weight. In some embodiments, the microbial oil comprises a sterol fraction of about 5% or less, about 4% or less, about 3% or less, about 2% or less, about 1.5% or less, or about 1% or less by weight.

In some embodiments, the microbial oil comprises a phospholipid fraction of at least about 2%, at least about 5%, or at least about 8% by weight. In some embodiments, the microbial oil comprises a phospholipid fraction of about 2% to about 25%, about 2% to about 20%, about 2% to about 15%, about 2% to about 10%, about 5% to about 25%, about 5% to about 20%, about 5% to about 20%, about 5% to about 10%, or about 7% to about 9% by weight.

In some embodiments, the microbial oil comprises a phospholipid fraction of less than about 20%, less than about 15%, less than about 10%, less than about 9%, or less than about 8% by weight. In some embodiments, the microbial oil is substantially free of phospholipids. In some embodiments, the microbial oil comprises unsaponifiables of less than about 2%, less than about 1.5%, less than about 1%, or less than about 0.5% by weight of the oil. The lipid classes present in the microbial oil, such as a triacylglycerol fraction, can be separated by flash chromatography and analyzed by thin layer chromatography (TLC), or separated and analyzed by other methods known in the art.

In some embodiments, the microbial oil and/or one or more fractions thereof selected from the triacylglycerol fraction, the free fatty acid fraction, the sterol fraction, the diacylglycerol fraction, and combinations thereof, comprises at least about 5%, at least about 10%, more than about 10%, at least about 12%, at least about 13%, at least about 14%, at least about 15%, at least about 16%, at least about 17%, at least about 18%, at least about 19%, at least about 20%, at least about 25%, at least about 30%, about least about 35%, at least about 40%, or at least about 45% by weight EPA. In some embodiments, the microbial oil and/or one or more fractions thereof selected from the triacylglycerol fraction, the free fatty acid fraction, the sterol fraction, the diacylglycerol fraction, and combinations thereof, comprises about 5% to about 55%, about 5% to about 50%, about 5% to about 45%, about 5% to about 40%, about 5% to about 35%, about 5% to about 30%, about 10% to about 55%, about 10% to about 50%, about 10% to about 45%, about 10% to about 40%, about 10% to about 35%, 10% to about 30%, at least about 12% to about 55%, at least about 12% to about 50%, at least about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 15% to about 25%, about 15% to about 20%, about 20% to about 55%, about 20% to about 50%, about 20% to about 45%, about 20% to about 40%, or about 20% to about 30% by weight EPA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises at least about 5%, at least about 10%, at least about 15%, at least about 20%, at least about 25%, at least about 30%, at least about 35%, at least about 40%, at least about 50%, or at least about 60% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% to about 60%, about 5% to about 55%, about 5% to about 50%, about 5% to about 40%, about 10% to about 60%, about 10% to about 50%, about 10% to about 40%, about 20% to about 60%, about 25% to about 60%, about 25% to about 50%, about 25% to about 45%, about 30% to about 50%, about 35% to about 50%, or about 30% to about 40% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 10% or less, about 9% or less, about 8% or less, about 7% or less, about 6% or less, about 5% or less, about 4% or less, about 3% or less, about 2% or less, or about 1% or less by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 1% to about 10%, about 1% to about 5%, about 2% to about 5%, about 3% to about 5%, or about 3% to about 10% by weight of the fatty acids as DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.1% to about 5%, about 0.1% to less than about 5%, about 0.1% to about 4%, about 0.1% to about 3%, about 0.1% to about 2%, about 0.2% to about 5%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% or less, less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5%, less than about 5%, about 4% or less, about 3% or less, about 2% or less, about 1% or less, about 0.75% or less, about 0.6% or less, or about 0.5% or less by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), stearidonic acid (18:4 n-3), or combinations thereof.

In another embodiment, microbial oil comprises omega-3 polyunsaturated fatty acids comprising DHA and EPA in an amount of about >90%, by weight, of the total amount of omega-3 polyunsaturated fatty acids, wherein the amount of EPA, by weight, is from about 10% to about 60% of the total amount of DHA and EPA, and the amount of DHA, by weight, is from about 40% to about 90% of the total amount of DHA and EPA.

Oil compositions of the invention include, but are not limited to, feed and food products, pharmaceutical compositions and cosmetics.

In some embodiments, the oil composition is an animal feed additive. An "animal" includes non-human organisms belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; or rodents such as mice, rats, hamsters and guinea pigs; and so on. An animal feed includes, but is not limited to, an aquaculture feed, a domestic animal feed including pet feed, a zoological animal feed, a work animal feed, a livestock feed, and combinations thereof.

In an embodiment of an animal feed additive, the total amount of omega-3 polyunsaturated fatty acids is at least about 400 mg per one gram of oil, preferably about 500 mg per one gram of oil, wherein the oil is a microbial oil.

In some embodiments of an animal feed additive, the microbial oil comprises from about 100 mg to about 300 mg EPA per one gram of oil and from about 200 mg to about 500 mg DHA per one gram of oil. In a still further embodiment, the microbial oil comprises a ratio of EPA:DHA of 1:1 to 1:30 or 1:1 to 1:5 by weight of total omega-3 polyunsaturated fatty acids.

A microbial oil according to the invention derives from a microbial biomass comprises cells, and preferably consists essentially of such cells, of the taxon Labyrinthulomycetes (Labyrinthulea, net slime fungi, slime nets), in particular those from the family of Thraustochytriaceae. The family of the Thraustochytriaceae (Thraustochytrids) includes the genera *Althomia, Aplanochytrium, Aurantiochytrium, Botryochytrium, Elnia, Japonochytrium, Oblongichytrium, Parietichytrium, Schizochytrium, Sicyoidochytrium, Thraustochytrium*, and *Ulkenia*. The biomass particularly preferably comprises cells from the genera *Aurantiochytrium, Oblongichytrium, Schizochytrium*, or *Thraustochytrium*, above all from the genus *Schizochytrium*.

In a very preferred embodiment of the current invention, cells, in particular a *Schizochytrium* strain, is employed which produces a significant amount of EPA and DHA, simultaneously, wherein DHA is preferably produced in an amount of at least 20 wt.-%, preferably in an amount of at least 30 wt.-%, in particular in an amount of 30 to 50 wt.-%, and EPA is produced in an amount of at least 5 wt.-%, preferably in an amount of at least 10 wt.-%, in particular in an amount of 10 to 20 wt.-% (in relation to the total amount of lipid as contained in the cells, respectively). DHA and EPA producing *Schizochytrium* strains can be obtained by consecutive mutagenesis followed by suitable selection of mutant strains which demonstrate superior EPA and DHA production and a specific EPA:DHA ratio. Any chemical or nonchemical (e.g. ultraviolet (UV) radiation) agent capable of inducing genetic change to the yeast cell can be used as the mutagen. These agents can be used alone or in combination with one another, and the chemical agents can be used neat or with a solvent.

Preferred species of microorganisms of the genus *Schizochytrium*, which produce EPA and DHA simultaneously in significant amounts, as mentioned before, are deposited under ATCC Accession No. PTA-10208, PTA-10209, PTA-10210, or PTA-10211, PTA-10212, PTA-10213, PTA-10214, PTA-10215.

A microbial oil according to the present invention can be manufactured according to a process a described below.

Manufacturing Process

An effective method of separating a polyunsaturated fatty acids (PUFAs) containing oil from the debris of a microbial biomass, comprising the following steps:

a) Providing a suspension of a biomass comprising cells which contain a PUFAs containing lipid;
b) Lysing the cells of the biomass;
c) Heating the suspension as obtained in step (b) to a temperature of 80° C. to 100° C., preferably 85° C. to 95° C., more preferably about 90° C., while adjusting the pH to a value of 9.5 to 11.5, preferably 10.0 to 11.0, more preferably 10.3 to 10.7;
d) Keeping the temperature and pH value in the ranges as depicted in (c) for at least 10 hours, preferably 15 to 40 hours, more preferably 20 to 36 hours.
e) Neutralization and separation of the oil from the biomass.

The steps (c) and (d) lead to the separation of the oil containing light phase and the water, cell debris, salts and residual oil containing heavy phase, as obtained by lysing the cells of the biomass. This separation of the light and heavy phase is also called "de-emulsification" or "demulsification" in the context of this application.

The order of the measures in step (d) is of no importance. Adjusting of the temperature can be carried out before or after adjusting the pH value.

Preferably, in the steps (b), (c) and (d) of the method the suspension is continuously mixed by using a stirrer and/or an agitator. In the method steps (c) and/or (d) preferably low shear agitation and/or axial-flow agitation is applied, in particular as disclosed in WO 2015/095694. Impellers suitable for agitating prior and during steps (c) and/or (d) include in particular straight blade impellers, Rushton blade impellers, axial flow impellers, radial flow impellers, concave blade disc impellers, high-efficiency impellers, propellers, paddles, turbines and combinations thereof.

Lysing of the cells of the biomass can be carried out by methods as known to those skilled in the art, in particular enzymatically, mechanically, physically, or chemically, or by applying combinations thereof.

Depending on the time of exposure and/or the degree of force applied, a composition comprising only lysed cells or a composition comprising a mixture of cell debris and intact cells may be obtained. The term "lysed lipids containing biomass" insofar relates to a suspension which contains water, cell debris and oil as set free by the cells of the biomass, but beyond that may also comprise further components, in particular salts, intact cells, further contents of the lysed cells as well as components of a fermentation medium, in particular nutrients. In a preferred embodiment of the invention, only small amounts of intact cells, in particular less than 20%, preferably less than 10%, more preferably less than 5% (relating to the total number of intact cells as present before lysing the cells of the biomass) are present in the lysed biomass after the step of lysing the cells.

Lysing of the cells may be realized for example by utilizing a French cell press, sonicator, homogenizer, microfluidizer, ball mill, rod mill, pebble mill, bead mill, high pressure grinding roll, vertical shaft impactor, industrial blender, high shear mixer, paddle mixer, and/or polytron homogenizer.

In a preferred embodiment, lysing of the cells comprises an enzymatic treatment of the cells by applying a cell-wall degrading enzyme. A cell-wall degrading enzyme is preferably selected from proteases, cellulases (e.g., Cellustar CL (Dyadic), Fibrezyme G2000 (Dyadic), Celluclast (Novozymes), Fungamyl (Novozymes), Viscozyme L (Novozymes)), hemicellulases, chitinases, pectinases (e.g., Pectinex (Novozymes)), sucrases, maltases, lactases, alpha-glucosidases, beta-glucosidases, amylases (e.g., Alphastar Plus (Dyadic); Termamyl (Novozymes)), lysozymes, neuraminidases, galactosidases, alpha-mannosidases, glucuronidases, hyaluronidases, pullulanases, glucocerebrosidases, galactosylceramidases, acetylgalactosaminidases, fucosidases, hexosaminidases, iduronidases, maltases-glucoamylases, xylanases (e.g., Xylanase Plus (Dyadic), Pentopan (Novozymes)), beta-glucanases (e.g., Vinoflow Max (Novozymes), Brewzyme LP (Dyadic)), mannanases, and combinations thereof. The protease may be selected from serine proteases, threonine proteases, cysteine proteases, aspartate proteases, metalloproteases, glutamic acid proteases, alcalases (subtilisins), and combinations thereof. The chitinase may be a chitotriosidase. The pectinase may be selected from pectolyases, pectozymes, polygalacturonases, and combinations thereof.

The enzyme is preferably added as a concentrated enzyme solution, preferably in an amount of 0.01 to 1.5 wt.-%, more preferably in an amount of 0.03 to 1.0 wt.-%, above all in an amount of 0.05 to 0.5 wt.-%, relating to the amount of concentrated enzyme solution as added in relation to the total amount of the suspension after addition of the concentrated enzyme solution.

In a further preferred embodiment of the process, after lysing the cells of the biomass and before the demulsification step, the suspension is concentrated to a total dry matter content of 30 to 60 wt.-%, more preferably 35 to 55 wt.-%, in particular 40 to 50 wt.-%.

Concentration of the suspension is preferably carried out by evaporation of water at a temperature not higher than 100° C., preferably 70° C. to 100° C., more preferably 80° C. to 90° C., until a total dry matter content of 30 to 60 wt.-% more preferably 35 to 55 wt.-%, in particular 40 to 50 wt.-%, is reached.

Concentration of the suspension is preferably carried out in a forced circulation evaporator (for example available from GEA, Germany) to allow fast removal of the water.

In general, adjusting the pH value can be carried out according to the invention by using either bases or acids as known to those skilled in the art. Decreasing of the pH can be carried out in particular by using organic or inorganic acids like sulfuric acid, nitric acid, phosphoric acid, boric acid, hydrochloric acid, hydrobromic acid, perchloric acid, hypochlorous acid, chlorous acid, fluorosulfuric acid, hexafluorophosphoric acid, acetic acid, citric acid, formic acid, or combinations thereof. As a high content of chloride is desirably avoided, in a preferred embodiment of the invention no or only small amounts of hydrochloric acid are used in the process of the current invention. According to the invention, sulfuric acid is the preferred substance for decreasing the pH value. —Increasing of the pH can be carried out in particular by using organic or inorganic bases like hydroxides, in particular sodium hydroxide, lithium hydroxide, potassium hydroxide, and/or calcium hydroxide, carbonates, in particular sodium carbonate, potassium carbonate, or magnesium carbonate, and/or bicarbonates, in particular lithium bicarbonate, sodium bicarbonate, and/or potassium bicarbonate. —Due to easiness of handling, the acids and bases are preferably used in liquid form, in particular as concentrated solutions. Thus, caustic soda is the preferred substance for increasing the pH value.

The method preferably comprises as a further step the harvesting of the PUFAs containing lipid from the demulsified composition as obtained in step (d).

The harvesting of the PUFAs containing lipid preferably comprises neutralization of the demulsified suspension and subsequent separation of the thus obtained oil containing light phase from the water, salts, cell debris and residual oil containing heavy phase.

Neutralization of the demulsified composition is preferably realized by adding an acid, preferably sulfuric acid, to adjust a pH value of 5.5 to 8.5, in particular 6.5 to 8.5, preferably 7.0 to 8.0. Before starting separation of the light phase from the heavy phase the thus obtained neutralized composition may be stirred at said pH value from several minutes up to several hours.

Separation of the oil containing light phase from the water, salts and cell debris containing heavy phase is preferably realized by mechanical means and preferably at a temperature of 60-90° C., more preferably 70-80° C., and at a pH value of preferably 6-9, more preferably 7-8.5. "Mechanical means" refers in particular to filtration and centrifugation methods as known to those skilled in the art.

After separation of the oil containing light phase, the PUFAs containing oil thus obtained can further be worked up by applying methods as known to those skilled in the art, in particular refining, bleaching, deodorizing and/or winterizing.

A particular advantage of the method is that by adjusting the pH prior to separation to less than 8.5, preferably less than 7.5, mitigation of free fatty acids to the aqueous phase of the oil (moisture) can be diminished such that the residual moisture of the oil contains less than about 8% preferably less than about 5% by weight of free fatty acid.

The methods of the current invention allow a very effective separation of the oil contained in the biomass from the cell-debris and other substances as contained in the fermentation broth. By using the methods of the current invention preferably more than 80 wt.-%, in particular more than 90 wt.-% of the oil contained in the biomass can be separated from the biomass and isolated.

It turned out that the oil as obtained by applying the method of the current invention has some advantageous characteristics over the PUFAs containing oils as disclosed in the state of the art so far. In particular it exhibits very low oxidation values, a low content of free fatty acids and impurities, a very low viscosity and a very high flash point.

The content of free fatty acids is determined in accordance with AOCS Official Method AOCS Ca 5a-40. The content of moisture is determined in accordance with AOCS Official Methods AOAC 930.15, 935.29. The content of insoluble impurities is determined in accordance with AOCS Official Method AOCS 3a-46. The amount of DHA and EPA is determined in accordance with AOCS Official Method AOCS Ce 1 b-89. The amount of total fat is determined in accordance with AOCS Official Method AOCS 996.06. The amount of crude fat is determined in accordance with AOCS Official Methods AOAC 920.39, 954.02.

EXAMPLES

Example 1: Production of a Microbial Oil

An unwashed cell broth containing microbial cells (*Schizochytrium* sp.) at a biomass density of over 100 g/l was heated to 60° C. in an agitated vessel. After heating up the suspension, the pH was adjusted to 7.5 by using caustic soda (50 wt.-% NaOH solution), before an alcalase (Alcalase® 2.4 FG (Novozymes)) was added in liquid form in an amount of 0.5 wt.-% (by weight broth). Stirring was continued for 3 hours at 60° C. After that, the lysed cell mixture was transferred into a forced circulation evaporator (obtained from GEA, Germany) and heated to a temperature of 85° C. The mixture was concentrated in the forced circulation evaporator, until a total dry matter content of about 30 wt.-% was reached. The concentrated lysed cell mixture was transferred into a new vessel, heated up to 90° C. under low shear agitation, while adjusting the pH to 10.5 by adding caustic soda. Low shear agitation was continued for about 30 hours, while keeping the temperature at 90° C. and the pH above 9.0 by adding caustic soda.

After that the resulting demulsified mixture was neutralized by adding sulfuric acid to adjust a pH of 7.5. Phase separation into a light phase, containing the oil, and a heavy phase, containing water, cell-debris, residual oil and salts, was carried out mechanically by using a disc stack separator (Alfa Laval Disc Stack Centrifuge, LAPX 404/Clara 20)

Due to the efficient demulsification, more than 90 wt.-% of the oil could be separated from the biomass without the addition of organic solvents or sodium chloride. And finally, the oil is effectively stable and does not show gelling properties. It contains less than 5% by weight of free fatty acid in the residual moisture of the oil.

Example 2—Microbial Oil as Animal Feed Additive

A specification of a microbial crude oil according to the invention for use as an animal feed additive in aquaculture is shown below.

| | |
|---|---|
| DHA + EPA, mg/g oil | min. 500 mg/g |
| DHA content, mg/g oil | min. 250 mg/g (mind 25% −> 40%) |
| EPA content, mg/g oil | min. 100 mg/g (mind 10% −> 25%) |
| Ratio EPA:DHA min | 1:4 |
| Ratio EPA:DHA max | 1:1 |
| Free fatty acid | max 5% |
| Moisture | max. 0.75% |
| DPA n-3 | <6 |
| Arachidonic Acid, % | <2 |
| Stearic acid, % | <2.5 |
| Palmitic acid, % | <30 |
| Crude Fat | >92% |

The invention claimed is:

1. An oil comprising:
   at least 25% by weight omega-3 polyunsaturated fatty acids (LC-PUFA), wherein
   the oil has a residual moisture content which comprises less than 5% by weight of free fatty acid in the residual moisture of the oil, and wherein
   the oil comprises at least 25% by weight docosahexaenoic acid (DHA), and at least 10% by weight eicosapentaenoic acid (EPA), and wherein
   the omega-3 polyunsaturated fatty acids are present in the oil in a total amount of at least 500 mg per one gram of oil.

2. The oil according to claim 1, wherein the moisture content of the oil is less than 2% by weight.

3. The oil according to claim 1, wherein the EPA is present in the oil in an amount from 100 mg to 250 mg EPA per one gram of oil, and the DHA is present in the oil in an amount from 250 mg to 400 mg DHA per one gram of oil.

4. The oil according to claim 3, wherein the oil comprises a weight ratio of the EPA:DHA of 1:1 to 1:30 based on total weight of the omega-3 polyunsaturated fatty acids.

5. The oil according to claim 1, wherein the oil is a plant oil.

6. The oil according to claim 1, wherein the oil is a microbial oil.

7. The oil according to claim 6, wherein the microbial oil is produced by Schizochytrium sp.

8. A microbial oil according to claim 6, wherein the residual moisture content of the oil is less than 2% by weight, and wherein the residual moisture comprises less than 5% by weight free fatty acids in the residual moisture.

9. The microbial oil according to claim 6, wherein the omega-3 polyunsaturated fatty acids are present in an amount from 400 mg to 800 mg per one gram of oil.

10. The microbial oil according to claim 6, wherein the oil comprises a weight ratio of the EPA:DHA from at least 1:1 based on total weight of the omega-3 polyunsaturated fatty acids.

11. The microbial oil according to claim 6, comprising at least 10% by weight of a triacylglycerol fraction, wherein
   at least 12% by weight of the fatty acids in the triacylglycerol fraction is eicosapentaenoic acid, and wherein
   at least 25% by weight of the fatty acids in the triacylglycerol fraction is docosahexaenoic acid, and wherein
   less than 5% by weight of the fatty acids in the triacylglycerol fraction is arachidonic acid.

* * * * *